US 9,429,540 B2

(12) United States Patent
Clyde et al.

(10) Patent No.: US 9,429,540 B2
(45) Date of Patent: Aug. 30, 2016

(54) LOW-TEMPERATURE ACTIVITY EXHAUST SENSOR

(75) Inventors: Eric P. Clyde, Metamora, MI (US); Walter T. Symons, Grand Blanc, MI (US); Kaius K. Polikarpus, Grand Blanc, MI (US); James D. Ward, Washington, DC (US); Marsha E. Nottingham, Howell, MI (US)

(73) Assignee: Delphi Technologies, Inc., Troy, MI (US)

( * ) Notice: Subject to any disclaimer, the term of this patent is extended or adjusted under 35 U.S.C. 154(b) by 242 days.

(21) Appl. No.: 13/698,449

(22) PCT Filed: Jun. 3, 2011

(86) PCT No.: PCT/US2011/039011
§ 371 (c)(1),
(2), (4) Date: Jan. 4, 2013

(87) PCT Pub. No.: WO2011/153402
PCT Pub. Date: Dec. 8, 2011

(65) Prior Publication Data
US 2013/0092538 A1    Apr. 18, 2013

Related U.S. Application Data

(60) Provisional application No. 61/351,323, filed on Jun. 4, 2010.

(51) Int. Cl.
  *G01N 27/416*  (2006.01)
  *G01N 27/407*  (2006.01)

(52) U.S. Cl.
  CPC ...... *G01N 27/4162* (2013.01); *G01N 27/4075* (2013.01)

(58) Field of Classification Search
  CPC ............ G01M 15/10; G01M 15/102; G01M 15/104; G01N 1/2252; G01N 27/404–27/407; G01N 27/409; G01N 27/419; G01N 27/4162; F02D 41/1483; F02D 41/1461; F02D 41/1474; F02D 41/146
  USPC .................................................. 204/421–429
  See application file for complete search history.

(56) References Cited

U.S. PATENT DOCUMENTS

| 4,441,981 | A | * | 4/1984 | Okamoto ........... G01N 27/4075 |
| | | | | 204/426 |
| 5,413,691 | A | * | 5/1995 | Kaneyasu et al. ............ 204/424 |
| 6,179,989 | B1 | | 1/2001 | Kennard, III et al. |
| 6,916,384 | B2 | | 7/2005 | Jain et al. |

OTHER PUBLICATIONS

International Search Report, PCT/US11/39011, Sep. 2011.

* cited by examiner

*Primary Examiner* — Jennifer Dieterle
(74) *Attorney, Agent, or Firm* — Joshua M. Davies

(57) ABSTRACT

An exhaust sensor comprises a sensing electrode and a reference electrode each in contact with an electrolyte. At least one of the sensing electrode and the reference electrode are formed by depositing an electrode precursor material on an electrolyte precursor material and sintering the combination at a sufficient temperature for a sufficient time to achieve densification of the electrolyte, wherein the electrode precursor material comprises an alkali salt. Electrode patterns having enhanced perimeter ratios are also disclosed. The resulting exhaust sensor is capable of providing a usable output at a reduced operating temperature.

7 Claims, 5 Drawing Sheets

LOW-TEMPERATURE ACTIVITY EXHAUST SENSOR

CROSS REFERENCE TO RELATED APPLICATIONS

This application claims priority to U.S. Provisional Application Ser. No. 61/351,253 filed Jun. 4, 2010, the contents of which are hereby incorporated by reference.

TECHNICAL FIELD

The present disclosure relates to an exhaust sensor that is capable of providing a usable signal at a reduced operating temperature.

BACKGROUND OF THE INVENTION

Exhaust oxygen sensors have been used for many years in vehicles to sense the presence of oxygen in the exhaust gas from the vehicle engine. The signal from the exhaust oxygen sensor may be used to provide a feedback signal to control the amount of fuel injected into the engine to minimize the production of undesirable exhaust emissions. The exhaust sensor must reach a certain minimum temperature in order to produce a usable signal. In order to minimize the time required for the sensor to reach its operating temperature, the industry trend has been to move toward planar sensing elements with co-fired electrodes and integral heating circuits. Due to their reduced size, planar sensors are capable of shorter time to activity, i.e. time required to reach a temperature at which a usable signal is available, compared to earlier conical sensing elements. It has been found that planar sensing elements are more susceptible to thermal shock cracking due to contact with water droplets that may be present in the vehicle exhaust system.

Accordingly, a need exists in the sensor art for sensors that are less susceptible to thermal shock cracking due to contact with water droplets.

SUMMARY

Disclosed herein is a planar sensor comprising a sensing electrode and a reference electrode, each in physical contact with an electrolyte. At least one of the sensing electrode and reference electrode are formed by depositing an electrode precursor material on an electrolyte precursor material and sintering the combination at a sufficient temperature for a sufficient time to achieve densification of the electrolyte. The electrode precursor material comprises an alkali salt in an amount sufficient to produce a sensor impedance after sintering less than 200 ohms at a sensor temperature at or below 450 degrees C.

Also disclosed herein is a planar sensor comprising a sensing electrode and a reference electrode, each in physical contact with an electrolyte. At least one of the sensing electrode and reference electrode are formed by depositing an electrode precursor material on an electrolyte precursor material and sintering the combination at a sufficient temperature for a sufficient time to achieve densification of the electrolyte. The electrode precursor material comprises an alkali salt in an amount sufficient to produce after sintering a sensor that can switch from providing a voltage less than 300 mv when exposed to lean exhaust to a voltage greater than 600 mv when exposed to rich exhaust at a sensor temperature at or below 450 degrees C.

The above described and other features are exemplified by the following figures and detailed description.

BRIEF DESCRIPTION OF THE DRAWINGS

Refer now to the Figures, wherein like elements are numbered alike.

DETAILED DESCRIPTION

At the outset of the description, it should be noted that the terms "first," "second," and the like, herein do not denote any order, quantity, or importance, but rather are used to distinguish one element from another, and the terms "a" and "an" herein do not denote a limitation of quantity, but rather denote the presence of at least one of the referenced items. The modifier "about" used in connection with a quantity is inclusive of the stated value and has the meaning dictated by the context (e.g., includes the degree of error associated with measurement of the particular quantity). It is noted that the terms "bottom" and "top" are used herein, unless otherwise noted, merely for convenience of description, and are not limited to any one position or spatial orientation. Furthermore, all ranges disclosed herein are inclusive and combinable (e.g., ranges of "up to about 25 weight percent (wt. %), with about 5 wt. % to about 20 wt. % desired, and about 10 wt. % to about 15 wt. % more desired," are inclusive of the endpoints and all intermediate values of the ranges, e.g., "about 5 wt. % to about 25 wt. %, about 5 wt. % to about 15 wt. %", etc.). Finally, unless defined otherwise, technical and scientific terms used herein have the same meaning as is commonly understood by one of skill in the art to which this invention belongs. The suffix "(s)" as used herein is intended to include both the singular and the plural of the term that it modifies, thereby including one or more of that term (e.g., the metal(s) includes one or more metals).

Figure 1:
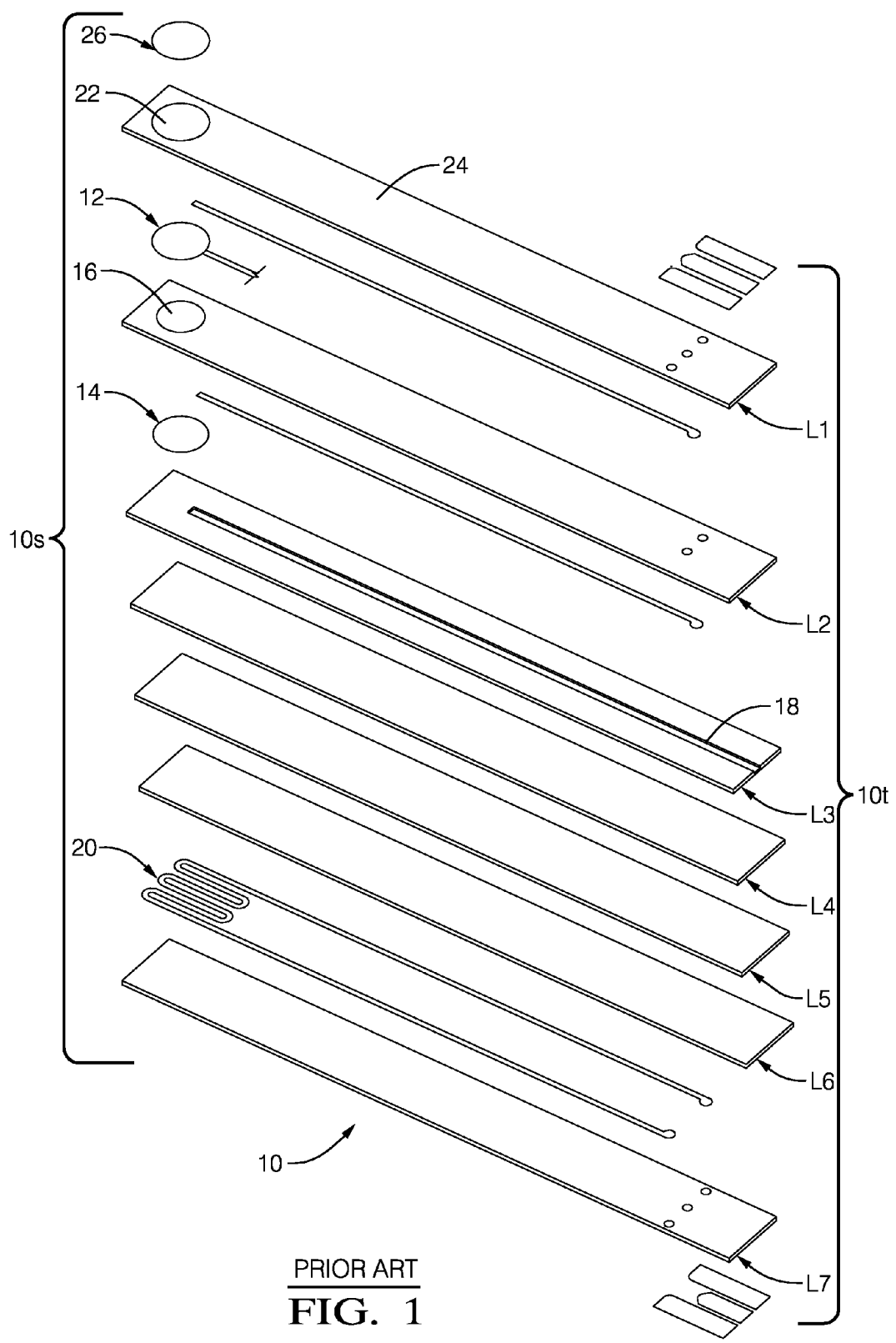
FIG. 1 is an exploded isometric view of an oxygen sensing element.

An exemplary planar oxygen-sensing element 10 is shown in FIG. 1. As shown in FIG. 1, sensing element 10 can comprise a sensing end 10s and a terminal end 10t. The sensing element 10 can comprise a sensing (i.e., first, exhaust gas, or outer) electrode 12, a reference gas (i.e., second or inner) electrode 14, and an electrolyte portion 16. The electrolyte portion 16 can be disposed at the sensing end 10s with the electrodes 12, 14 disposed on opposite sides of, and in ionic contact with, the electrolyte portion 16, thereby creating an electrochemical cell (12/16/14).

A reference gas channel 18 can be disposed on the side of the reference electrode 14 opposite the electrolyte portion 16. The reference gas channel 18 can be disposed in fluid communication with the reference electrode 14 and with a reference gas (e.g., the ambient atmosphere or another gas supply).

A heater 20 can be disposed on a side of the reference gas channel 18 opposite the reference electrode 14, for maintaining sensing element 10, and in particular, the sensing end 10s of the sensing element, at a desired operating temperature. The heater 20 can be any heater capable of maintaining the sensor end 10s at a sufficient temperature to facilitate the various electrochemical reactions therein. The heater 20 can be, for example, Pt, Pd, and the like, as well as oxides, mixtures, and alloys comprising at least one of the foregoing metals. Optionally, the heater can be one of the electrically conductive element(s). The heater 20 can be disposed on one of the support layers by various methods such as, for example, screen-printing. The thickness of the heater 20 can be about 5 micrometers to about 50 micrometers, or so.

A protective layer L1 can be disposed adjacent to the sensing electrode 12 opposite the electrolyte portion 16. The protective layer L1 can comprise a solid portion 24 and a porous portion 22 disposed adjacent to the sensing electrode 12. The porous portion 22 can be a material that enables fluid communication between the sensing electrode 12 and the gas to be sensed. For example, the porous portion 22 can comprise a porous ceramic material formed from a precursor comprising a ceramic (e.g., spinel, alumina, zirconia, and/or the like), a fugitive material (e.g., carbon black), and an organic binder. The fugitive material can provide pore formation in the fired layer. The porous portion 22 can be formed, for example, from a precursor comprising about 70 to about 80 weight percent (wt. %) of one or more of the foregoing ceramic materials, about 5 to about 10 wt. % of the fugitive material, and about 15 wt. % to about 20 wt. % of an organic binder, based upon the total weight of the precursor, which can be applied using various methods including thick film methods, and the like, followed by sintering.

In order to further protect the sensing electrode 12, a protective coating 26 can optionally be disposed over the porous portion 22 and optionally over layer L1. As with the porous portion 22, at least in the area of the porous portion 22, the protective coating 26 allows fluid communication between the sensing electrode 12 and the gas to be sensed. Possible materials for the protective coating 26 can comprise spinel, alumina (e.g., stabilized alumina), and other protective coatings employed in sensors.

If desired, one or more support layers can be disposed on a side of the sensing electrode 12 opposite the electrolyte 16; between the reference gas channel 18 and the heater 20, and on a side of the heater 20 opposite the reference gas channel 18. As shown, insulating layer L1 is disposed on a side of the sensing electrode 12 opposite the electrolyte portion 16; support layers L3-L6 are disposed between the reference electrode 14 and the heater 20; and support layer L7 is disposed on a side of the heater 20 opposite the reference gas channel 18. A support layer L2 can be employed with the electrolyte 16 disposed therethrough, attached to an end thereof, or the electrolyte can comprise the entire layer.

The support layers, e.g., L2-L7, that can provide structural integrity (e.g., protect various portions of the gas sensor from abrasion and/or vibration, and the like, and provide physical strength to the sensor); physically separate and electrically isolate various components; and provide support for various components that can be formed in or on the layers. Depending on the arrangement, the support layers can each comprise the same or different materials, e.g., a dielectric material (e.g., alumina ($Al_2O_3$)), an electrolytic material (e.g., zirconium oxide (zirconia)), protective material, and the like. Each of the support layers can comprise a thickness of up to about 500 micrometers or so, depending upon the number of layers employed, or, more particularly, about 50 micrometers to about 200 micrometers. Although illustrated herein as comprising seven layers L1-L7, it should be understood that the number of layers could be varied depending on a variety of factors.

Electrolyte portion 16 can comprise a solid electrolyte. The electrolyte portion 16 can be disposed through layer L2 in a variety of arrangements. For example, the entire layer L2 can be formed of electrolyte material 16. Alternatively, the electrolyte portion 16 can be attached to L2 at the sensing end such that the electrolyte portion 16 forms the sensing end of L2, disposed in an aperture (not illustrated) adjacent to the sensing end 10s, and disposed in an opening through the layer L2. The latter arrangement eliminates the use of excess electrolyte. Any shape can be used for the electrolyte, with the size and geometry of the various inserts, and therefore the corresponding openings, being dependent upon the desired size and geometry of the adjacent electrodes. The openings, inserts, and electrodes can comprise a substantially compatible geometry such that sufficient exhaust gas access to the electrode(s) is enabled and sufficient ionic transfer through the electrolyte is established to attain the desired sensor function. The electrolyte can comprise a thickness of up to about 500 micrometers or so, more specifically, about 25 micrometers to about 500 micrometers, and even more specifically, about 50 micrometers to about 200 micrometers.

The electrolyte 16 can be, for example, any material that is capable of permitting the electrochemical transfer of oxygen ions while inhibiting the passage of exhaust gases, desirably has an ionic/total conductivity ratio of approximately unity, and is compatible with the environment in which the sensor will be utilized. Possible electrolyte materials can comprise any material capable of functioning as a sensor electrolyte including, but not limited to, zirconium oxide (zirconia), cerium oxide (ceria), calcium oxide, yttrium oxide (yttria), lanthanum oxide, magnesium oxide, ytterbium (III) oxide ($Yb_2O_3$), scandium oxide ($Sc_2O_3$), and so forth, as well as combinations comprising at least one of the foregoing. If zirconia is employed, it can be stabilized with, for example, with calcium, barium, yttrium, magnesium, aluminum, lanthanum, cesium, gadolinium, and so forth, as well as combinations comprising at least one of the foregoing materials. For example, the electrolyte can be alumina stabilized zirconia and/or yttrium stabilized zirconia.

Accordingly, formation of electrically conductive element(s) of the sensing element 10 can comprise preparing a suitable precursor material such as an ink, paste, slurry and/or the like. For example, a precursor (ink) can be formed by mixing a metal powder with a sufficient quantity of an organic vehicle to attain the desired adhesion to the substrate after firing, as well as other properties.

Optionally, the precursor material can comprise a metal oxide, for example, to improve the adhesion of the electrically conductive element(s) to underlying substrate (where applicable), and/or impart beneficial properties such as inhibition of further sintering. Possible metal oxides can comprise ceria, lanthana, magnesia, zirconia, yttria, alumina, scandia, and the like, and mixtures comprising at least one of the foregoing. The amount of metal oxide employed is dependent upon the particular metals employed and the temperatures used in forming the sensor. The metal powder and optional metal oxide can be combined with a vehicle (e.g., an organic vehicle) to enable deposition of the precursor onto the desired portion(s) of the sensor element.

Once prepared, the conductive element precursor material can be applied to the desired area of the sensor, using various application technique(s) such as thick film technique(s) including screen printing, painting, spraying, dipping, coating, and the like. Depending upon the particular electrically conductive element, as well as the particular technique employed, optional thickener(s), binder(s), additive(s), fugitive material(s) (e.g., carbon, insoluble organic material, and the like), and so forth (hereinafter additive(s)), can be employed in the precursor material in an amount of less than or equal to about 40 wt. % additives for screen printing, less than or equal to about 60 wt. % additives for pad flexing (painting), less than or equal to about 75 wt. % additives for spray coatings, less than or equal to about 90 wt. % additives for dip coatings, based on the total weight of thick film inks. Possible additives include: 1-ethoxypropan-2-ol, turpentine, squeegee medium, 1-methoxy-2-propanol acetate, butyl acetate, dibutyl phthalate, fatty acids, acrylic resin, ethyl cellulose, pine oil, 3-hydroxy, 2,2,4-trimethylpentyl isobutyrate, terpineol, butyl carbitol acetate, cetyl alcohol, cellulose ethylether resin, and so forth, as well as combinations comprising at least one of the foregoing.

The thickness of the electrically conductive elements (e.g., the leads, the heater, the contact pads, temperature sensor, the vias, and other electrically conductive components) is dependent upon the particular element. The thickness can be up to the thickness of the layer or so (e.g., for a via), or, more particularly, about 1 micrometers (μm) to about 50 micrometers, or, even more particularly, about 3 micrometers to about 35 micrometers, and still more particularly about 7 micrometers to about 25 micrometers.

Furthermore, the element precursor material can be applied during any point during the manufacturing process; i.e., before the substrate is fired (green), before the substrate is fully fired (bisque), or after the substrate is fully fired. In each case, once the element precursor material has been applied, the substrate is heated to a temperature sufficient to sinter the precursor material (e.g., greater than or equal to about 1450° C. for about 2 hours). Optionally, the electrically conductive elements can be co-fired with green layers (alumina ($Al_2O_3$), zirconia ($ZrO_2$), and so forth). For a coating comprising a metal oxide such as zirconia, alumina, for example, temperatures of about 1,400° C. or greater can be employed.

The foregoing sensor, and others comprising a different number of cells, can be formed using a variety of methods in which the components can be formed and fired separately or formed (optionally laminated), and co-fired. For example, an electrolyte tape can be formed and partially fired to the bisque state. The precursor material can be prepared as described above and deposited on the appropriate portions of the support layer(s) and/or the electrolyte tape and connecting electrical leads to the ink. A protective layer and support layer(s) can be disposed accordingly, with a temperature sensor and/or heater disposed therein as desired. The lay-up can then be heated to a sufficient temperature to volatilize the organics and to sinter the metals in the precursor, thereby forming the sensor.

Figure 2:
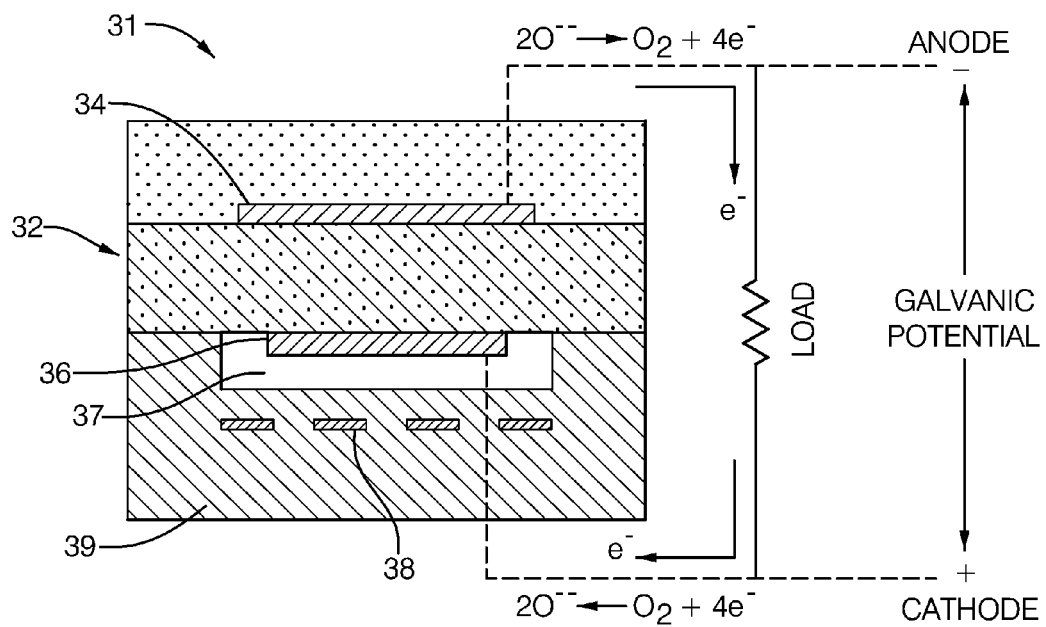
FIG. 2 is a schematic of a galvanic cell using zirconia as an oxygen ion electrolyte.

FIG. 2 shows a schematic diagram of a galvanic cell as formed within the sensor as described with respect to FIG. 1. FIG. 2 shows a schematic of a galvanic cell 31 using zirconia as an oxygen ion electrolyte 32 as is typically found in sensor elements such as those described with reference to FIG. 1. In addition to an anode 34 and a cathode 36, the cell can comprise an air channel 37, an alumina layer 39 and a heater 38. A thin membrane of partially stabilized zirconia 32 separates the two gas atmospheres having oxygen partial pressures $P_{O2}^{ref}$ and $P_{O2}^{exhaust}$. Each surface of the zirconia membrane has a co-fired noble metal containing electrode that promotes the chemical reactions:

$O_2 + 4e^- \rightarrow 2O^{-2}$ Reference electrode 14 (Cathode 36)
$2O^{-2} \rightarrow O_2 + 4e^-$ Sensing electrode 12 (Anode 34)

It is to be noted that cathode 36 in FIG. 2 corresponds functionally to reference electrode 14 in FIG. 1, and that anode 34 in FIG. 2 corresponds to sensing electrode 12 in FIG. 1.

At temperatures below about 600° C., performance of the sensor element often deteriorates (e.g., reduced voltage amplitude, lean shift, low and asymmetric response times, etc.). These performance problems are due, at least in part, to low electrolyte conductivity, high electrode impedance, and low catalytic activity of the anode and cathode electrodes 34, 36 (sensing electrode 12 and reference electrode 14). It has been found that including alkali salts in the precursor material used to form the electrodes 12, 14 results in a sensor that is capable of providing a usable sensor output at a reduced temperature. Not to be bound by any theory, it is thought that the use of alkali salts influences the degree of sintered grain growth experienced during co-firing of the electrodes 12, 14 and the electrolyte 16. It has been found that optimal performance has been achieved using potassium salts. The combination of potassium and fully yttria-stabilized zirconia in the electrode material yields an electrode material which has more active sites and is more specific to the oxygen content in exhaust gas emissions, and thus promotes stronger signals with less lean shift at lower temperatures. Fully yttria-stabilized (8 mole percent) zirconium oxide is included in the range of 6-10 weight percent, with 7.50% being exemplary in the current formulation. Yttrium oxide is added in the range of 0.5 to 3.0 weight percent, with 1.0 weight percent being an exemplary formulation. The potassium is added in various forms and methods to a final concentration of 3,000 to 10,000 ppm, with 5,000 to 8,000 ppm being preferred, and 6,500 ppm being an exemplary formulation. Functional performance comparisons between electrodes with and without alkali additives demonstrate the advantage to the composition, as is seen in the following examples.

While it has been determined that adding a potassium salt to the electrode precursor material is advantageous, it has also been determined that further improvement in sensor response characteristics can be obtained by modifying the geometry of the sensing electrode 12 and the reference electrode 14.

In FIG. 1, the sensing electrode 12 and the reference electrode 14 are depicted as having circular shapes. It has been determined that alternative geometries for the electrodes 12, 14 can result in improved sensor response. These alternative geometries will be discussed in terms of a parameter that will be referred to as "perimeter ratio". As used herein, the term perimeter ratio means the ratio of the total perimeter of the shape or shapes that define the extent of the electrode pattern divided by the perimeter of the smallest rectangle that can enclose the electrode pattern.

Figure 3:
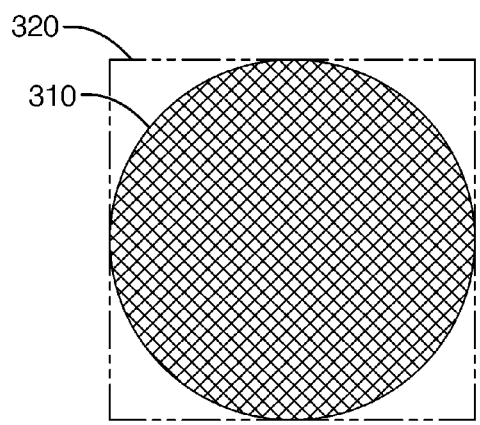
FIGS. 3A and 3B are electrode patterns used to illustrate the concept of perimeter ratio as used herein.
Figure 3:
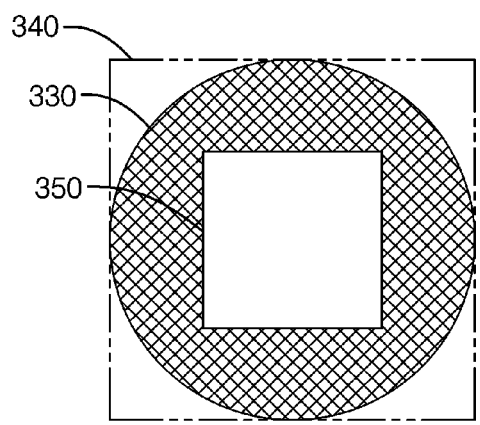

FIGS. 3A and 3B illustrate the concept of perimeter ratio as used herein. It is to be noted that the patterns shown in FIGS. 3A and 3B are presented to illustrate the definition of perimeter ratio as used herein, and are not represented to be actual electrode patterns that were investigated in the development of the present invention. In FIG. 3A, the cross-hatched circle 310 represents the pattern of electrode metallization, and the square 320 represents the smallest rectangle that can enclose the circle 310. If the circle 310 has a radius R, the area of the circle is $\pi R^2$ and the perimeter of the circle is its circumference, which is $2\pi R$. The square 320 has sides that measure 2R, and has a perimeter of 8R. The perimeter ratio as defined herein is the ratio ($2\pi R/8R$), which is equal to $\pi/4$.

In FIG. 3B, an alternate electrode pattern 330 is shown. The pattern 330 is defined as a circle with radius R having an open square area 350 internal to the circle, where the square has sides each equal to R, the radius of circle 330. In FIG. 3B, area of the electrode pattern 330 is the area of the circle ($\pi R^2$) minus the area of the square ($R^2$), which equals ($\pi-1)R^2$. The perimeter of the pattern 330 is the sum of the perimeter of the circle (2nR) and the perimeter of the internal square 350 (4R). The bounding rectangle 340 is a square having sides that each measure 2R with a perimeter of 8R. For the pattern 330 shown in FIG. 3B, the perimeter ratio would be calculated as ($2\pi R+4R)/8R$, which is equal to ($\pi+2)/4$.

Figure 4:
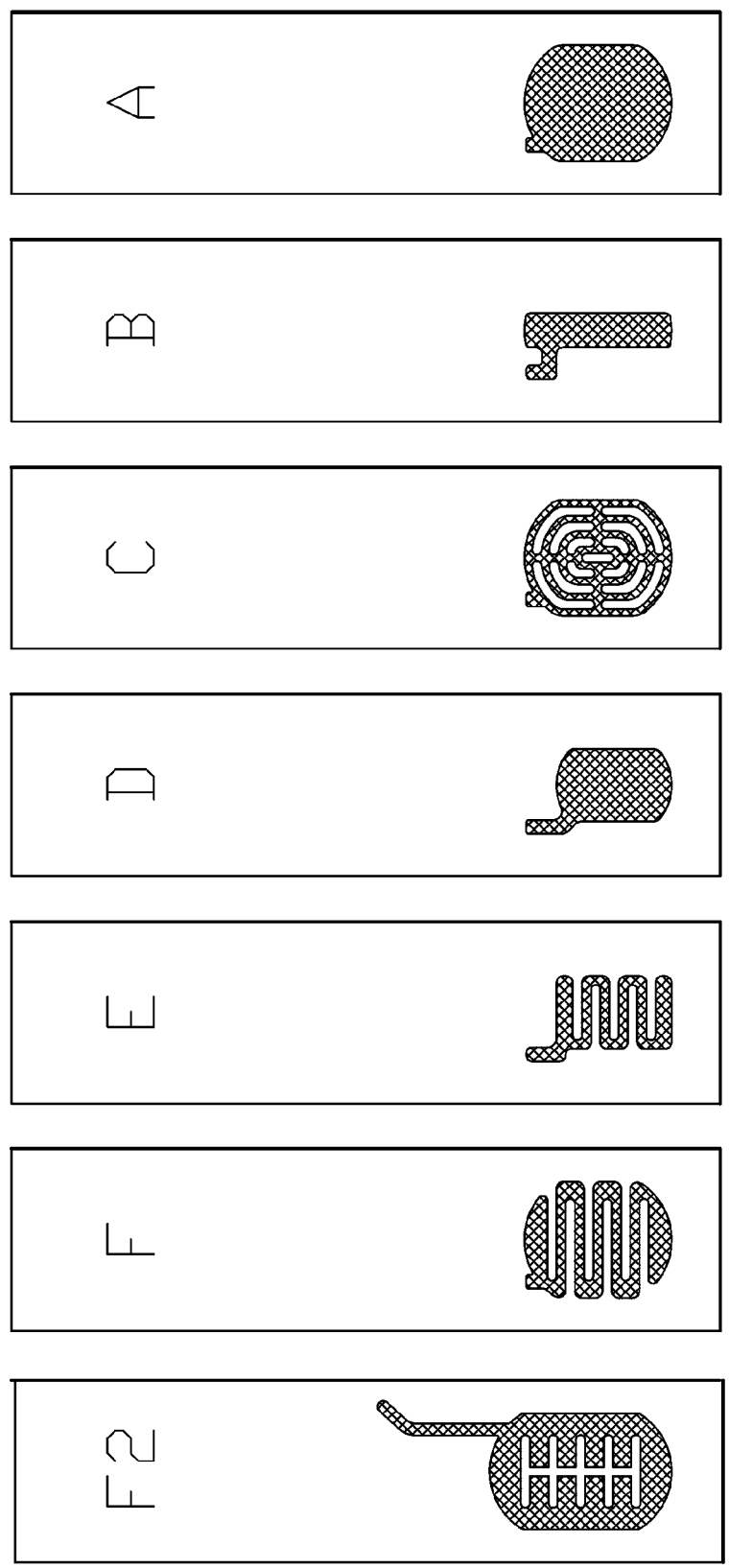
FIG. 4 is an illustration of alternative electrode geometries.

FIG. 4 illustrates several electrode geometries that were evaluated in the development of this invention. The area and perimeter of several of these patterns are listed in the table below.

| Electrode Pattern | Electrode Area (mm$^2$) | Electrode Perimeter (mm) | Dimensions of bounding rectangle (mm) | Perimeter of bounding rectangle (mm) | Perimeter ratio |
|---|---|---|---|---|---|
| A | 7.174 | 10.007 | 3.200 × 2.550 | 11.500 | 0.870 |
| B | 2.689 | 9.414 | 3.200 × .750 | 7.900 | 1.192 |
| C | 3.937 | 45.085 | 3.200 × 2.550 | 11.500 | 3.920 |
| D | 4.004 | 9.156 | 2.500 × 1.600 | 8.200 | 1.117 |
| E | 2.804 | 22.581 | 2.500 × 1.600 | 8.200 | 2.754 |
| F | 4.544 | 33.979 | 3.200 × 2.550 | 11.500 | 2.955 |
| F2 | 7.132 | 29.897 | 3.950 × 2.550 | 13.000 | 2.300 |

It has been determined that increasing the perimeter ratio for a given electrode area improves the performance of the exhaust sensor. Without being bound by any theory, it is believed that catalytic reactions occur at the boundary between the platinum electrode material and the zirconia electrolyte. Increasing the perimeter ratio of the electrode increases the opportunity for gas exchange at these boundaries. It is also believed that the perimeter ratio affects the steady state performance of the sensor, and the total electrode area affects the transient response performance of the sensor.

The following examples are merely to further illustrate the sensor element and/or the electrode(s), and are not intended to limit the scope thereof.

EXAMPLES

Electrode Impedance

The electrochemical cell in the exhaust sensor can be considered as a voltage source with an associated source impedance. The impedance is a function of temperature, decreasing with increasing sensor temperature. It is desirable for the sensor to have a low impedance, with a maximum value of 200 ohms being a typical target value.

Figure 5:
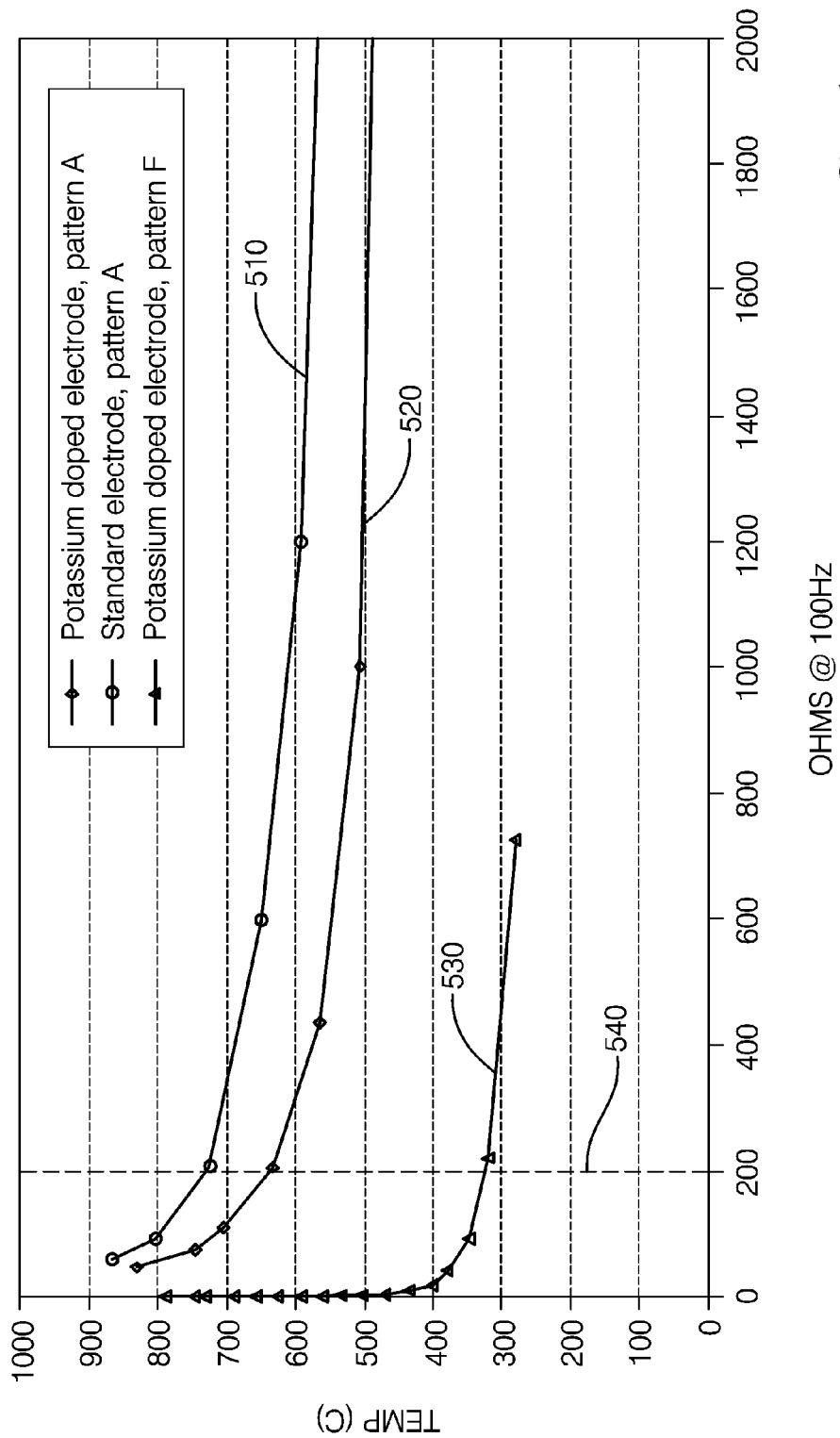
FIG. 5 is a chart of sensor impedance vs. temperature for several electrode compositions and geometries.

FIG. 5 presents experimental results relating impedance to sensor temperature for samples prepared with different electrode formulations and different electrode patterns. Trace 510 in FIG. 5 represents the characteristics of a sensor fabricated using a standard electrode material (no added potassium) with the electrodes shaped as pattern "A" in FIG. 4. Trace 520 represents the characteristics of a sensor fabricated using an electrode material which included potassium, with the electrodes shaped as pattern "A" in FIG. 4. Trace 530 represents the characteristics of a sensor fabricated using an electrode material which included potassium, with the electrodes shaped as pattern "F" in FIG. 4. FIG. 5 also includes a line 540 which represents a target maximum impedance value of 200 ohms. As demonstrated by FIG. 5, the sensor represented by trace 510 requires an operating temperature in excess of 700° C. to have an impedance less than the 200 ohm target value. Changing the electrode material to include potassium, as represented by trace 520, results in an improvement in required operating temperature, as the 200 ohm target value is achieved at a temperature between 600 and 650° C. Further changing the sensor fabrication to use the potassium doped electrode material in conjunction with changing the electrode pattern to "F" in FIG. 4, which has a higher perimeter ratio, a sensor was obtained as shown in trace 530 having an impedance below the 200 ohm target at a temperature well below 400° C. The sensor represented by trace 530 in FIG. 5 can achieve a targeted low impedance at a reduced operating temperature compared to the sensors represented by traces 510 and 520, thus offering less susceptibility to thermal shock induced by water droplets in the exhaust gas.

Sensor Output Voltage

The exhaust sensor acts as an electrochemical cell that provides a voltage that is a function of the oxygen concentration in the exhaust gas, with a lower voltage when the oxygen concentration in the exhaust gas is higher and a higher voltage when the oxygen concentration is lower. A parameter that is used to characterize the nature of the exhaust gas is called the excess air ratio, represented by the Greek letter Lambda ($\lambda$). Lambda is defined as the ratio of the actual engine air/fuel ratio to the stoichiometric air/fuel ratio. Lambda is greater than 1.00 for lean air/fuel mixtures and less than 1.00 for rich air/fuel mixtures. Exhaust sensors can be characterized by exposing them to a gas mixture, perturbing the gas mixture between values of $\lambda<1.00$ and $\lambda>1.00$, and observing the sensor output as Lambda is changed. For a given value of Lambda, the voltage produced by the exhaust sensor depends on the temperature of the sensor.

Figure 6:
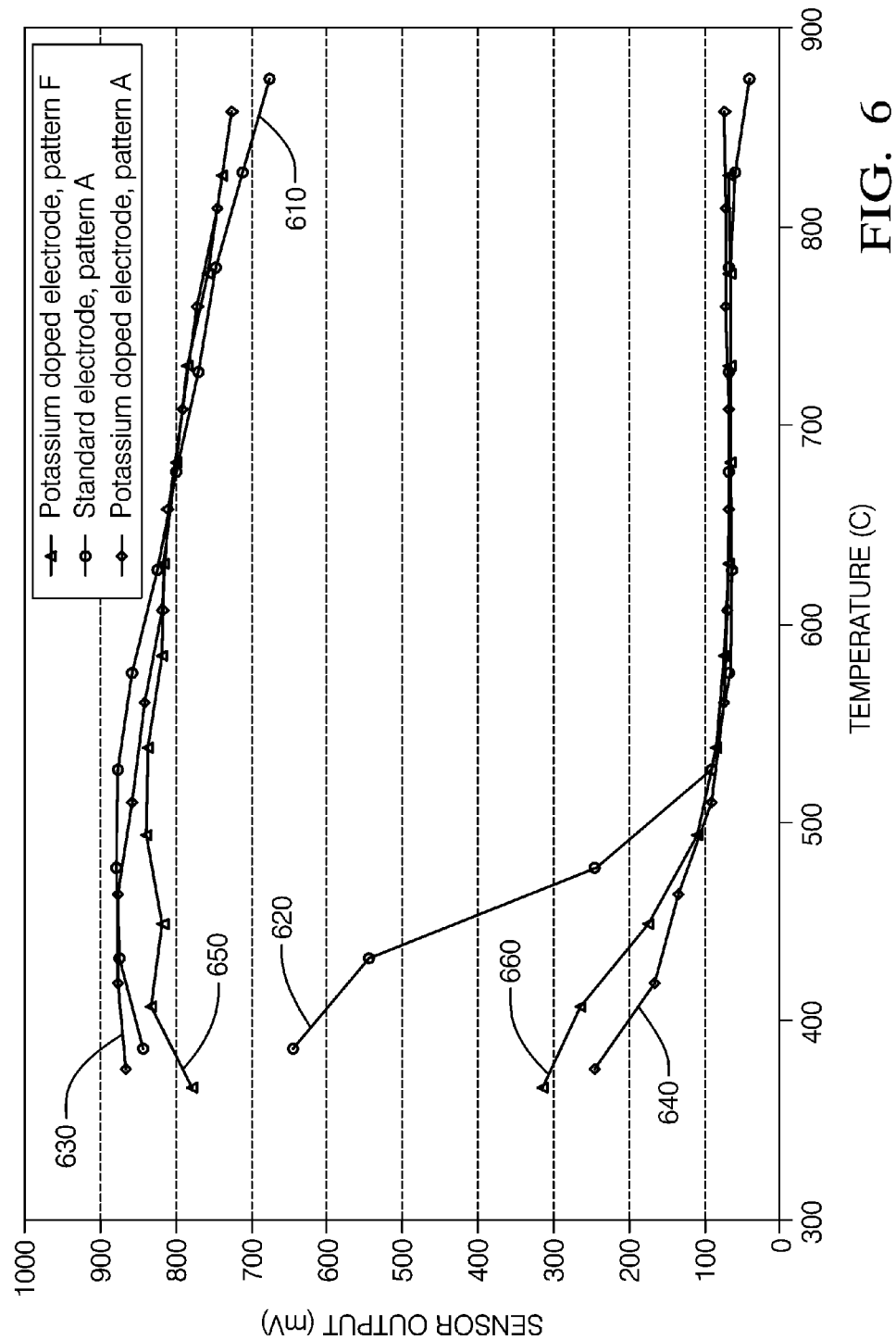
FIG. 6 is a chart of sensor output voltage vs. temperature for several electrode compositions and geometries.

FIG. 6 presents test results relating output voltage to sensor temperature, under both rich and lean conditions. In this test a number of sensors were exposed to an exhaust gas mixture which was perturbed from $\lambda=0.98$ to $\lambda=1.02$ at a 1 Hz perturbation rate. The exhaust gas temperature was 260° C., and the sensor temperature was further controlled by applying heater voltages from 7 to 17 volts in 1 volt steps. Each sensor was thermocoupled so that the exact sensor temperature could be recorded. Typical target performance for an exhaust sensor is a rich voltage above 600 mv and a lean voltage below 300 mv.

Trace 610 in FIG. 6 depicts the rich performance of a sensor fabricated using a standard electrode material (no added potassium) with the electrodes shaped as pattern "A" in FIG. 4, and trace 620 depicts the lean performance of the same sensor. Trace 610 shows that this sensor met the target of rich voltage above 600 mv over the entire temperature range tested, but trace 620 shows that the target of a lean voltage below 300 mv was only met for sensor temperatures in excess of 450° C.

Trace 630 in FIG. 6 depicts the rich performance of a sensor fabricated using an electrode material which included potassium, with the electrodes shaped as pattern "A" in FIG. 4, and trace 640 depicts the lean performance of the same sensor. These traces show that this sensor met both the target of rich voltage above 600 mv and the target of lean voltage below 300 mv over the entire temperature range tested.

Trace 650 represents the rich performance of a sensor fabricated using an electrode material which included potassium, with the electrodes shaped as pattern "F" in FIG. 4, and trace 660 depicts the lean performance of the same sensor. While both traces show some minor degradation in the lower temperature performance of the sensor, this sensor was still able to meet the target performance of 600 mv rich voltage and 300 mv lean voltage even at temperatures as low as 450° C.

As demonstrated by the above examples, an exhaust sensor with electrodes formed from an electrode precursor material doped with an alkali salt and having a modified electrode geometry can provide improved impedance and output voltage characteristics at reduced operating temperatures. By reducing the sensor operating temperature, improved resistance to thermal shock cracking due to water droplets in the exhaust gas contacting the sensor can be obtained.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation of material to the teachings of the invention without departing from the essential scope thereof. Therefore, it is intended that the invention not be limited to the particular embodiments disclosed as including the best mode contemplated for carrying out this invention, but that the invention will include all embodiments falling within the scope of the appended claims.

What is claimed is:

1. An exhaust sensor comprising a sensing electrode and a reference electrode each in physical contact with an electrolyte;
    wherein at least one of the sensing electrode and the reference electrode are formed by depositing an electrode precursor material configured as a pattern on an electrolyte precursor material and sintering the combination at a sufficient temperature for a sufficient time to achieve densification of the electrolyte,
    wherein the electrode precursor material comprises an alkali salt,
    wherein the perimeter ratio of at least one of the sensing electrode and the reference electrode is greater than unity by an amount sufficient to produce a sensor impedance after sintering less than 200 ohms at a sensor temperature at or below 450 degrees C.

2. The exhaust sensor of claim 1, wherein the electrode precursor material additionally comprises yttria-stabilized zirconia.

3. The exhaust sensor of claim 1, wherein the alkali salt is a potassium salt.

4. An exhaust sensor comprising a sensing electrode and a reference electrode each in physical contact with an electrolyte;
    wherein at least one of the sensing electrode and the reference electrode are formed by depositing an electrode precursor material configured as a pattern on an electrolyte precursor material and sintering the combination at a sufficient temperature for a sufficient time to achieve densification of the electrolyte,
    wherein the electrode precursor material comprises an alkali salt in an amount sufficient to produce after sintering a sensor that can switch from providing a voltage less than 300 my when exposed to lean exhaust to a voltage greater than 600 my when exposed to rich exhaust at a sensor temperature at or below 450 degrees C.

5. The sensor of claim 4, wherein the electrode precursor material additionally comprises yttria-stabilized zirconia.

6. The sensor of claim 4, wherein the alkali salt is a potassium salt.

7. The sensor of claim 4, wherein the perimeter ratio of at least one of the sensing electrode and the reference electrode is greater than unity by an amount sufficient to produce a sensor impedance after sintering less than 200 ohms at a sensor temperature at or below 450 degrees C.

* * * * *